United States Patent [19]

Showalter et al.

[11] Patent Number: 4,755,469
[45] Date of Patent: Jul. 5, 1988

[54] OIL TRACING METHOD

[75] Inventors: William E. Showalter, Seal Beach; Elihu Goldish, Lakewood; Ronald J. Lukasiewicz, Irvine, all of Calif.

[73] Assignee: Union Oil Company of California, Los Angeles, Calif.

[21] Appl. No.: 423,698

[22] Filed: Sep. 27, 1982

[51] Int. Cl.$^4$ .............................................. G01N 33/28
[52] U.S. Cl. ........................................ 436/27; 436/30; 436/56
[58] Field of Search .................. 436/27, 30, 56, 82, 436/83, 84; 356/70

[56] References Cited

U.S. PATENT DOCUMENTS

| | | |
|---|---|---|
| 3,526,127 | 9/1970 | Sarkis ...................................... 356/70 |
| 3,719,453 | 3/1973 | Erdman . |
| 3,755,189 | 8/1973 | Gilchrist et al. . |
| 3,976,428 | 8/1976 | Link ...................................... 436/111 |
| 3,977,963 | 8/1976 | Readal et al. . |
| 3,993,131 | 11/1976 | Riedel ...................................... 436/27 |
| 4,075,085 | 2/1978 | Young . |
| 4,264,329 | 4/1981 | Beckett ...................................... 436/27 |

OTHER PUBLICATIONS

Greenkorn; Experimental Study of Waterflood Tracers, J. of Petroleum Tech., Jan. '62, pp. 87–92.
Hackh's Chemical Dictionary, McGraw-Hill Book Co., 1944, pp. 332–333.
Kirk-Othmer, Encyclopedia of Chemical Technology, 1979 (5), pp. 339–368.
Altwicker, Elmar R.; Brodsky, Ira S.; Shen, Thomas T.; American Chemical Society, Division of Fuel Chemistry, Preprint, 1974, 19 (1), 99–110, Chem. Abstracts.
Japanese Pat. No. 74 42,886 to Ogawa; Chem. Abstracts.
Korsakova, I. S.; Shpiro, G. S.; Neftepererab, Neftekhim (Moscow), 1976; Chemical Abstracts.

Primary Examiner—Barry S. Richman
Assistant Examiner—Michael S. Gzybowski
Attorney, Agent, or Firm—Howard Lambert; G. Wirzbicki; D. Sandford

[57] ABSTRACT

A method for tagging an oil so that subsequently it may be identified as to source by incorporating into the oil as a tracer material an oil-soluble or oil-dispersible Group VIB, Group VIIB or lanthanum series rate earth metal salt of a fatty acid. The so-tagged oil may be utilized in any desired manner. Thereafter, an oil suspected to contain at least a portion of the so-tagged oil is analyzed for the presence of the added metal moiety. The method is especially useful in tracing a complex oleaginous and petroliferous material so that it may be recovered and identified following a theft or spill or to trace the flow of such oil injected through a subterranean reservoir.

25 Claims, No Drawings

OIL TRACING METHOD

BACKGROUND OF THE INVENTION

1. Field of the Invention

This invention relates to a method for tagging an oleaginous and petroliferous substance so that it subsequently may be identified as to source. More particularly, the invention relates to such a method wherein control of the so-tagged substances is temporarily lost, as when they are stolen, spilled, misplaced or injected into a subterranean reservoir.

2. Description of the Prior Art

Sometimes one has in his control a first oleaginous and petroliferous substance. This control can then be lost, either deliberately, as when an oil is injected into a subterranean reservoir in an enhanced oil recovery process or in an oil disposal process, or inadvertently, as when an oil is spilled or stolen. Subsequently, there can come within one's control a second oleaginous substance which is suspected either to be or to contain a portion of the first oleaginous substance. This second oleaginous substance may be oil produced from a subterranean reservoir, discovered under circumstances arousing suspicion that it may be oil previously stolen or spilled, or encountered in any of a number of other circumstances.

Such oleaginous substances are difficult to identify. Some oleaginous and petroliferous substances, such as crude oil, have such a complex structure that their compositions are difficult to define and distinguish from each other. Other such substances, such as fractions of refined crude oil, have compositions so much alike that one sample from one source is difficult to distinguish from another sample from a different source. In either of the above instances, tracing a given sample of oil whose origin is unknown back to its source can prove onerous.

One instance in which control of an oil is lost is when the oil is injected into a subterranean petroleum-bearing reservoir. A typical reservoir is a stratum of rock containing tiny interconnected pore spaces which are saturated with oil, water and/or gas. When one or more wells are drilled into such a reservoir, fluids can be introduced into or withdrawn from the reservoir. This flow of fluid causes the indigenous reservoir fluids to migrate through the reservoir. Sometimes, as in enhanced oil recovery processes, plugging processes or waste disposal processes, fluids are injected into the reservoir via one well and simultaneously or subsequently fluids are produced from the reservoir via the same or a different well. It is often desired to determine whether the fluids produced contain any of the fluids which were injected. Such information is important in determining the permeability and porosity of the reservoir and the fluid flow characteristics through the reservoir.

It is known to add a tracer material to an injected fluid and to examine a produced fluid for the presence of the tracer material. Numerous materials have been suggested as tracer materials including radioactive materials, such as Iodine[131], and other chemical compounds which are not commonly present in reservoir fluids in significant concentrations and are therefore easily detectable in small concentrations by conventional analytical techniques.

Most fluids injected into reservoirs during the above-described processes have been aqueous base fluids. Hence, the tracers employed have been water-soluble materials. However, it is sometimes desired to inject an oil into a reservoir and trace its flow through the reservoir. An oil or oil base enhanced oil recovery fluid has certain advantages over water base fluids used for this purpose. An oil base fluid is generally more compatible with reservoir oil and rock than is a water base fluid. Reservoirs sometimes contain clays which are substantially unaffected by oil but which swell when contacted by water. Such swelling can sharply decrease the permeability of a reservoir. In studying the flow characteristics through a reservoir, it is sometimes desired to inject an oil containing a tracer material into the reservoir via one well, produce fluids from the reservoir via one or more offset wells and examine the produced fluid to determine if any of the injected oil is present. In disposing of an oil or an oil base fluid in a reservoir, it is convenient to include in the fluid being disposed of an oil-soluble tracer material so that fluid movement through the reservoir can be monitored.

Therefore, it is a principal object of this invention to provide a method for tracing an oil.

It is a further object to provide such a method wherein an oil-soluble tracer material is added to a first oil, control of the first oil is lost, and subsequently a second oil is located and analyzed for the presence of the tracer added to the first oil.

It is a still further object to provide such a method for investigating the dynamic conditions of fluid flow through a subterranean reservoir penetrated by one or more wells.

It is another object to provide such a method wherein a fluid is injected into the reservoir and its flow through the reservoir is monitored.

It is yet another object to provide such a method wherein an oil or an oil base fluid containing a tracer material is injected into the reservoir via one well, reservoir fluids are produced via the same or a different well and the produced fluids are analyzed for the presence of the tracer material.

Other objects, advantages and features of this invention will become apparent to those skilled in the art from the following description and appended claims.

SUMMARY OF THE INVENTION

Briefly, the invention provides a method for tracing a first oil comprising (1) adding to the first oil a minor amount of an oil-soluble or oil-dispersible tracer material comprising a Group VIB, Group VIIB or lanthanum series rare earth metal salt of a fatty acid having 5 to 35 carbon atoms, (2) utilizing the first oil, (3) recovering a second oil suspected to be or to contain a portion of the utilized first oil, and (4) analyzing the second oil for the metal component of the tracer material by a conventional analytical technique, as for example, an atomic spectrometry method.

In an alternate embodiment of the invention, the invention provides a method for investigating the dynamic conditions of fluid flow in a permeable subterranean reservoir penetrated by one or more wells wherein there is injected into the reservoir via one well an oil or an oil base fluid containing a minor amount of the tracer material, fluids are produced from the reservoir via the same or another well, and the produced fluid is analyzed for the presence of the injected metal.

Another particular embodiment of the invention provides a method for tagging an oil with the tracer material so that if control of the oil is lost, a subsequently recovered oil can be analyzed to determine if it contains the metal component of the tracer material.

DETAILED DESCRIPTION OF THE INVENTION

In studying or utilizing permeable petroleum bearing subterranean reservoirs penetrated by one or more wells, it is often desired to inject an oil or an oil base fluid into the reservoir via one well, produce fluids from the reservoir via the same or a different well and determine whether or not any of the injected fluid is contained in the produced fluid. This objective can be achieved by including in the injected fluid an oil-soluble or oil-dispersible tracer material which is not naturally present in a significant concentration in the reservoir fluids, and analyzing the produced fluids for the tracer material. Similarly, if one has control of a first oil, adds such a tracer material to the first oil, loses control of the first oil, subsequently comes into control of a second oil, and analyzes the second oil for the tracer material, it can be established whether or not the second oil is or contains a portion of the first oil.

The particular tracer material of this invention is a Group VIB, Group VIIB or lanthanum series rare earth metal salt of a fatty acid having about 5 to 35 carbon atoms. While the amount of tracer material to be used can vary considerably with such factors as the exact method in which it is to be used, the nature of the oil injected or the first oil, the nature of the reservoir fluids, the distance through the reservoir which the tracer material-containing oil passes, and the particular analytical technique employed, in general, about 10 to 5,000, preferably 25 to 2,500 weight parts per million of the rare earth metal added as the salt of a fatty acid, based on the weight of the oil to be injected, or the first oil, is employed.

Considering the metal component of the tracer material, the Group VIB metals of the periodic chart of the elements are chromium, molybdenum and tungsten. The Group VIIB metals are manganese, technetium and rhenium. The lanthanum series rare earths include, in addition to lanthanum, cerium, praseodymium, neodymium, promethium, samarium, europium, gadolinium, terbium, dysprosium, holmium, erbium, thulium, ytterbium and lutetium. None of these metals is present in a significant concentration in most reservoir fluids or oils. As a further guide in determining which metal to employ in a particular application, a sample of the natural reservoir fluid or the first oil can be obtained and analyzed for its Group VIB, Group VIIB and lanthanum rare earth metal content. Any of these metals not present in a significant concentration in the reservoir fluid or the first oil can be selected for inclusion in the tracer material.

The fatty acids containing about 5 to 35 carbon atoms which make up part of the metal salts used in this invention include (1) carboxylic acids of the alkanoic series from pentanoic acid to pentatriacontanoic acid; (2) carboxylic acids of the alkenoic series from 2-,3-, or 4-pentenoic acid to cis-21-triacontenoic acid; (3) polyunsaturated aliphatic monocarboxylic acids such as sorbic, linoleic, linolenic and eleostearic acids; (4) substituted fatty acids such as 2-ethylhexanoic and ricinoleic acids; and (5) aromatic carboxylic acids such as benzoic, salicylic, cinnamic and gallic acids. The individual fatty acids can be relatively expensive. Since what is desired in the fatty acid moiety of the tracer material is oil solubility, rather than any particular fatty acid, it is preferred to use a relatively inexpensive mixture of fatty acids, such as naphthenic acid. Naphthenic acids are carboxylic acids that are derived from petroleum during the refining of the various distilled fractions and are predominately monocarboxylic acids. The main distinguishing feature of naphthenic acids is a hydrocarbon chain consisting of single or fused cyclopentane rings, which are alkylated in various positions with short aliphatic groups. Other acids, e.g., aliphatic, dicarboxylic, and those containing the cyclohexane ring, also are present in moderate quantities.

Preferred tracer materials include manganese naphthenate, chromium naphthenate, and molybdenum naphthenate. Other preferred manganese compounds include manganese linoleate, manganese octoate, manganese oleate, manganese rosinate and manganese tallate.

The tracer material can be added directly to the oil to be injected or the first oil, either batchwise accompanied by agitation or continuously as when the oil is being injected down a well. Since the amount of tracer material employed is small compared with the amount of oil to be injected, it is preferred to prepare a concentrated solution of the tracer material in an organic solvent. Generally about 2 to 30, preferably about 4 to 15, parts by weight metal added as the salt of a fatty acid per 100 parts by weight organic solvent can be used.

The organic solvent can be any such solvent which is soluble or dispersible in the oil or oil base material to be injected or the first oil. Suitable organic solvents include crude oil, a fraction of a crude oil, an aliphatic hydrocarbon such as pentane or hexane, or an aromatic hydrocarbon such as benzene, toluene or xylene.

To detect the metal component of the tracer material in a produced fluid, any common analytical technique can be employed. Due to their sensitivity and ease of use, it is preferred to use an atomic spectrometry method. These methods include atomic absorption, atomic emission, plasma emission spectrometry, flame atomic absorption, X-ray fluorescence and neutron activation.

Especially preferred is either flame or flameless atomic absorption spectroscopy. In flameless atomic absorption, a metered portion of a sample is disposed in a graphite tube. The graphite tube is heated to a high temperature by electric current. The sample is thus decomposed and vaporized (atomized), whereby the elements of the sample are present in the graphite tube in their atomic states in a "cloud of atoms". In flame atomic absorption the sample is introduced into the flame as an aerosol and atomization takes place. Next, in either flame or flameless atomic absorption, a measuring beam, consisting of light having the resonance wavelength of the element of interest, is absorbed in accordance with the quantity of the element in the sample, as each element in its atomic state absorbs its resonance wavelength only. The spectra produced have very sharp lines that are specific for each element.

The invention is further illustrated by the following example which is illustrative of various aspects of the invention and is not intended as limiting the scope of the invention as defined by the appended claims.

EXAMPLE

Large volumes of crude oil are produced from a subterranean reservoir during the testing of an experimental production technique utilizing a remotely located production well. There is no practical means of transporting the produced crude oil to a refinery or other point of utilization. In order to dispose of the produced crude oil, it is necessary to reinject it back into the reservoir via an offset injection well. In order to properly evaluate the production technique, it is preferred that there be no communication between the production well and the injection or disposal well, i.e., the produced crude oil should not contain any crude oil previously produced and reinjected. The produced crude oil is analyzed using an atomic adsorption spectrophotometer Model 306 marketed by Perkin-Elmer Corporation and found to contain 0.6 part per million of manganese. 10,000 barrels of the produced crude oil are reinjected back into the reservoir via an offset injection well. As the crude oil is being pumped down the injection well, there is blended into the oil as a tracer material 0.0175 pound manganese per barrel of crude oil. The manganese-containing composition is a solution of 32° API mineral spirits containing 6 percent by weight of manganese added as manganese naphthenate. Thus, the reinjected crude oil contains 50 parts per million of manganese. Subsequently, the production well is again produced for six months. The additional produced crude oil is periodically analyzed for manganese content using an atomic adsorption spectrophotometer. Throughout this six month period of additional production, the manganese content of the crude oil varies from 0.58 to 0.61 parts per million manganese. These results indicate that none of the reinjected crude oil containing the tracer material has migrated through the reservoir from the disposal well to the production well.

While various specific embodiments and modifications of this invention have been described in the foregoing specification, further modification will be apparent to those skilled in the art. Such further modifications are included within the scope of this invention as defined by the following claims:

We claim:

1. A method for tracing a first oleaginous and petroliferous substance comprising:
   (a) incorporating into a first oleaginous and petroliferous substance an oil-soluble or oil-dispersible tracer material comprising a metal salt of an acid selected from the group consisting of:
      (1) carboxylic acids of the alkanoic series having 5 to 35 carbon atoms;
      (2) carboxylic acids of the alkenoic series having 5 to 30 carbon atoms;
      (3) polyunsaturated aliphatic monocarboxylic acids;
      (4) naphthenic acids; and
      (5) mixtures of two or more of the foregoing;
      said metal selected from the group consisting of Group VIB metals, Group VIIB metals, and lanthanum series rare earth metals;
   (b) utilizing the first oleaginous and petroliferous substance in a manner so that control thereof is lost;
   (c) obtaining a second oleaginous and petroliferous substance suspected to be or to contain a portion of the first oleaginous and petroliferous substance; and
   (d) analyzing the second oleaginous and petroliferous substance for the presence of the metal moiety of the trace material.

2. The method defined in claim 1 wherein there is added to the oleaginous and petroliferous substance about 10 to 5,000 weight parts per million based on the amount of the first oleaginous and petroliferous substance of the metal component added as a metal salt.

3. The method defined in claim 1 wherein the tracer material is added as a concentrated solution in an organic solvent.

4. The method defined in claim 1 wherein the metal is manganese.

5. The method defined in claim 1 wherein the tracer material is manganese naphthenate.

6. The method defined in claim 1 wherein the first oleaginous and petroliferous substance is utilized by injecting the same into a subterranean reservoir.

7. The method defined in claim 1 wherein the acid is a mixture of acids.

8. The method defined in claim 7 wherein the mixture of acids is naphthenic acids.

9. The method defined in claim 1 wherein the second oleaginous and petroliferous substance is analyzed for the metal moiety of the tracer material by an atomic spectrometry method.

10. The method defined in claim 9 wherein the atomic spectrometry method is atomic absorption.

11. A method for investigating the dynamic conditions of fluid flow in a permeable subterranean reservoir penetrated by one or more wells comprising:
   (a) injecting into a subterranean reservoir via one well a slug of a first oleaginous and petroliferous substance having incorporated therein an oil-soluble or oil-dispersible tracer material comprising a metal salt of an acid having 5 to 35 carbon atoms and selected from the group consisting of carboxylic acids of the alkanoic series, carboxylic acids of the alkenoic acid series, polyunsaturated aliphatic monocarboxylic acids, and naphthenic acids, said metal selected from the group consisting of Group VIB metals, Group VIIB metals, and lanthanum series rare earth metals;
   (b) subsequently producing from the subterranean reservoir via the same or a different well a slug of a second oleaginous and petroliferous substance; and
   (c) analyzing the second oleaginous and petroliferous substance for the presence of the metal moiety of the tracer material.

12. The method defined in claim 11 wherein there is added to the oleaginous and petroliferous substance about 10 to 5,000 weight parts per million based on the amount of the first oleaginous and petroliferous substance of the metal component added as a metal salt.

13. The method defined in claim 11 wherein the tracer material is added as a concentrated solution in an organic solvent.

14. The method defined in claim 11 wherein the metal is manganese.

15. The method defined in claim 11 wherein the tracer material is manganese naphthenate.

16. The method defined in claim 11 wherein the first oleaginous and petroliferous substance is utilized by injecting the same into a subterranean reservoir.

17. The method defined in claim 11 wherein the acid is a mixture of acids.

18. The method defined in claim 17 wherein the mixture of acids is naphthenic acids.

19. The method defined in claim 11 wherein the second oleaginous and petroliferous substance is analyzed for the metal moiety of the tracer material by an atomic spectrometry method.

20. The method defined in claim 19 wherein the atomic spectrometry method is atomic absorption.

21. A method for tracing a first oleaginous and petroliferous substance, comprising:
(a) incorporating into a first oleaginous and petroliferous substance an oil-soluble or oil-dispersible tracer comprising a metal salt of a substituted or unsubstituted acid containing about 5 to 35 carbon atoms, selected from the group consisting of carboxylic acids of the alkanoic series, carboxylic acids of the alkenoic series, polyunsaturated aliphatic monocarboxylic acids and naphthenic acids, said metal selected from the group consisting of Group VIB metals, Group VIIB metals, and lanthanum series rare earth metals;
(b) utilizing the first oleaginous and petroliferous substance, into which the tracer has been incorporated, in a manner so that control of the substance is lost;
(c) obtaining a second oleaginous and petroliferous substance, suspected to be or to contain a portion of the first oleaginous and petroliferous substance; and
(d) analyzing the second oleaginous and petroliferous substance to determine the presence of the tracer.

22. The method defined in claim 21 wherein about 10 to about 5,000 weight parts per million of the tracer is incorporated into the first substance.

23. The method defined in claim 21 wherein the tracer is manganese naphthenate.

24. The method defined in claim 21 wherein the second substance is analyzed by an atomic spectrometry method.

25. The method defined in claim 24 wherein the atomic spectrometry method is atomic absorption.

* * * * *